United States Patent
Hunkeler et al.

(10) Patent No.: US 9,545,480 B2
(45) Date of Patent: Jan. 17, 2017

(54) SYRINGE ASSEMBLER METHOD (71) Applicant: FISHER CLINICAL SERVICES GMBH, Allschwil (CH)

(72) Inventors: Guido Hunkeler, Schonenbuch (CH); Joerg Spettl, Lorrach (DE)

(73) Assignee: Fisher Clinical Services, GMBH, Allschwil (CH)

( * ) Notice: Subject to any disclaimer, the term of this patent is extended or adjusted under 35 U.S.C. 154(b) by 341 days.

(21) Appl. No.: 14/454,525

(22) Filed: Aug. 7, 2014

(65) Prior Publication Data
US 2016/0038685 A1 Feb. 11, 2016

(51) Int. Cl.
*B21D 53/00* (2006.01)
*A61M 5/34* (2006.01)
*A61M 5/315* (2006.01)
*A61M 5/00* (2006.01)
*A61M 5/32* (2006.01)
*G01L 9/00* (2006.01)
(Continued)

(52) U.S. Cl.
CPC ......... *A61M 5/31515* (2013.01); *A61M 5/002* (2013.01); *A61M 5/3202* (2013.01); *A61M 5/34* (2013.01); *B21D 53/00* (2013.01); *G01L 9/0089* (2013.01); *G01M 11/081* (2013.01); *A61M 2205/3306* (2013.01); *A61M 2207/00* (2013.01); *A61M 2207/10* (2013.01); *A61M 2209/02* (2013.01); *G01B 11/14* (2013.01); *G01N 21/84* (2013.01); *Y10T 29/4978* (2015.01); *Y10T 29/49778* (2015.01)

(58) Field of Classification Search
CPC A61M 5/34; A61M 5/31515; A61M 2207/10; A61M 5/3202; A61M 2209/02; Y10T 29/4978; Y10T 29/49778; Y10T 29/49769; B21D 53/00; B23Q 17/22; G01N 21/84; G01N 2001/247; G01N 21/95; H04N 7/18
USPC ........ 348/86, 92, 94, 95, 210, 217, 218, 219
See application file for complete search history.

(56) References Cited

U.S. PATENT DOCUMENTS 2,592,381 A 4/1952 Blackman
2013/0242082 A1 9/2013 Miller

FOREIGN PATENT DOCUMENTS

DE 2008004421 B3 4/2009
EP 1 920 793 A1 5/2008

OTHER PUBLICATIONS

International Search Repot and Written Opinion dated Jan. 7, 2016, issued in PCT Application No. PCT/IB2015/001762, filed Jul. 28, 2015.

(Continued)

*Primary Examiner* — Jermie Cozart
(74) *Attorney, Agent, or Firm* — Workman Nydegger (57) ABSTRACT

A method for assembling a syringe includes supporting a syringe barrel having a stopper being movably disposed therein. A distal end of a plunger rod is inserted into the compartment of the syringe barrel. An initial digital image is taken of the stopper within the syringe barrel. The distal end of the plunger rod is coupled to the stopper located within the syringe barrel so that the plunger rod is secured to the stopper. A plurality of further digital images of the stopper within the syringe barrel are taken during or after coupling the distal end of the plunger rod to the stopper. Information determined from each of the further digital images is compared to information determined from the initial digital image using a computer processor to determine if the stopper in each of the further digital images has moved relative to the syringe barrel.

15 Claims, 8 Drawing Sheets

(51) Int. Cl.
*G01M 11/08* (2006.01)
*G01N 21/84* (2006.01)
*G01B 11/14* (2006.01)

(56) References Cited

OTHER PUBLICATIONS

*The Growth & Benefits of Pre-filled Syringes: What Clinical Teams Should Know About Precision Assembly & Labeling*, Fisher Clinical Services, Inc., published on-line between Apr. 1, 2014 and Aug. 6, 2014, pp. 26.

SYRINGE ASSEMBLER METHOD

CROSS-REFERENCE TO RELATED APPLICATIONS

Not applicable.

BACKGROUND OF THE INVENTION

1. The Field of the Invention

The present invention relates to methods and systems for attaching plunger rods to stoppers within pre-filled syringe barrels so as to ensure that the plunger rods are properly attached to the stoppers and to ensure that there has been no movement of the stoppers during the attachment that could potentially jeopardize the sterility of the liquid dosage housed within the syringe barrels.

2. The Relevant Technology

Clinical trials for some pharmaceutical drugs require that the drug dosage be delivered by injection through the use of a syringe. As part of the clinical trial protocols, the syringes are preloaded with a single dose of the drug or a placebo prior to shipping and use. As part of the preloading process, the plunger rod for each syringe is typically attached to a corresponding syringe stopper after the dosage and stopper have been placed within the syringe barrel. In this procedure, however, care must be taken so that no excessive movement of the stopper relative to the syringe barrel occurs while the plunger rod is being attached to the stopper. Excessive movement of the stopper relative to the syringe barrel can potentially result in contamination of the dosage.

In one approach to detecting whether the stopper has moved during the attachment of the plunger rod, a first digital image of the stopper is taken prior to attaching the plunger rod and a second digital image of the stopper is taken after the plunger rod is fully attached to the stopper. Information from the two digital images is compared to determine whether the stopper in the second digital image has moved relative to the stopper in the first digital image. If movement of the stopper is detected that is outside of a defined limit, the syringe and corresponding dosage are rejected and subsequently disposed of.

Although the above process is useful, it has some shortcomings. For example, the above process only detects movement of the stopper relative to its initial position and does not detect movement of the stopper relative to the syringe barrel. Thus, if the syringe barrel also moves between taking the first digital image and the second digital image, it is possible, depending upon the direction of movement and the length of movement, that the results deduced from the two digital images could either: 1) fail to detect when a stopper has moved beyond its defined limit relative to the syringe barrel, and should thus be rejected, or 2) determine that the stopper has moved beyond the defined limit and thus reject the syringe and dosage when in fact the stopper has not moved beyond the defined limit relative to the syringe barrel. Furthermore, conventional monitoring systems only determine if there has been movement of the stopper after the plunger rod has been fully attached. As such, the conventional systems do not account for movement of the stopper during attachment of the plunger rod where the stopper returns to its original position by the end of the attachment process. Other shortcomings also exist with current monitoring systems.

Accordingly, what is needed in the art are methods and systems that overcome all or some of the shortcomings of conventional monitoring systems.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

In the following detailed description, reference is made to the accompanying drawings, which form a part hereof. In the drawings, similar symbols typically identify similar components, unless context dictates otherwise. The embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein. It will also be understood that any reference to a first, second, etc. element in the claims or in the detailed description is not meant to imply numerical sequence, but is meant to distinguish one element from another unless explicitly noted otherwise.

Furthermore, multiple instances of an element may each include separate letters appended to the element number. For example two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

In addition, as used in the specification and appended claims, directional terms, such as "top," "bottom," "up," "down," "upper," "lower," "proximal," "distal," "horizontal," "vertical," and the like are used herein solely to indicate relative directions and are not otherwise intended to limit the scope of the invention or claims.

The present invention generally relates to methods and systems for attaching plunger rods to stoppers within pre-filled syringe barrels so as to ensure that the plunger rods are properly attached to the stoppers and to ensure that there has been no movement of the stoppers during the attachment that could potentially jeopardize the sterility of the liquid dosage housed within the syringe barrels. The methods and systems can be used in association with syringes for dispensing drugs in clinical trials but other applications are also applicable.

Figure 1:
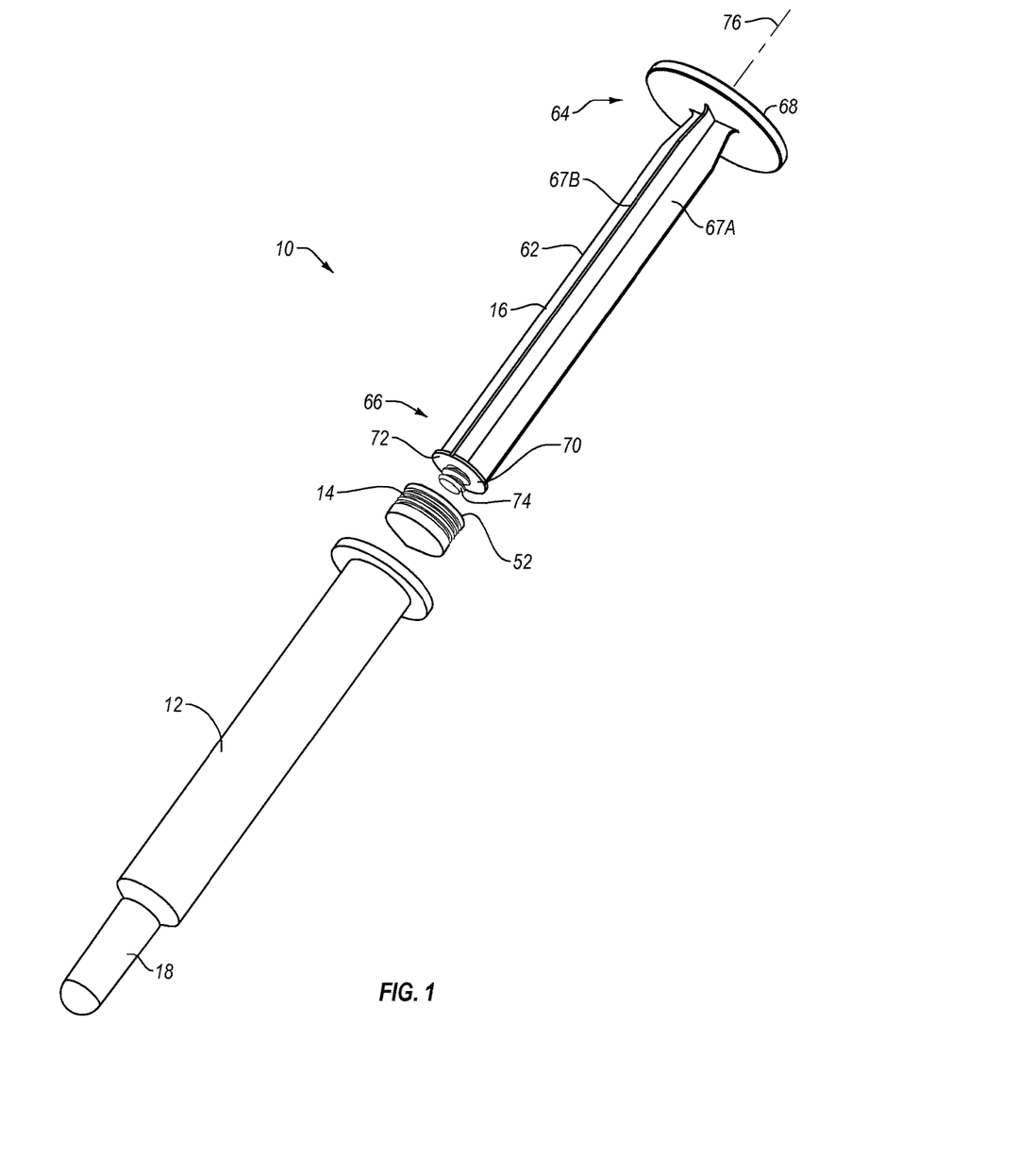
FIG. 1 is a partially exploded view of a syringe.

Depicted in FIG. 1 is one embodiment of a conventional syringe 10 that can be used in association with the present invention. In general, syringe 10 comprises a syringe barrel 12, a needle 36 (FIG. 2) extending from a dispensing end of syringe barrel 12, a needle shield 18 that covers needle 36, a stopper 14 that is received within syringe barrel 12, and a plunger rod 16 that couples with stopper 14. The above elements will now be discussed in greater detail.

Figure 2:
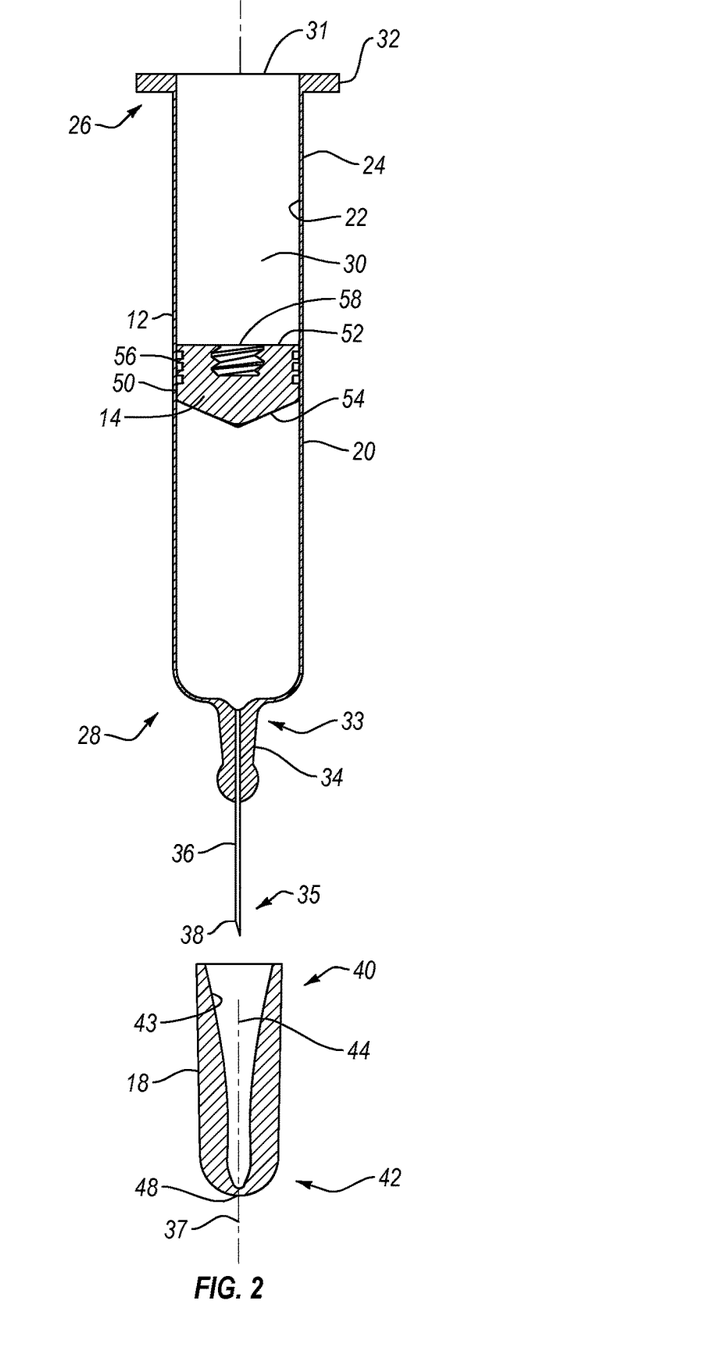
FIG. 2 is a partially exploded, cross-sectional side view of the syringe barrel, stopper, needle and needle shield shown in FIG. 1.

As depicted in FIG. 2, syringe barrel 12 comprises an elongated cylindrical body 20 having an interior surface 22 and an exterior surface 24 that longitudinally extend between a loading end 26 and an opposing dispensing end 28. Interior surface 22 bounds a compartment 30 that extends between opposing ends 26 and 28. An opening 31 is formed at the loading end 26 and communicate with compartment 30. A flange 32 radially outwardly projects from loading end 26. Flange 32 can encircle loading end 26 or can project out from opposing sides of loading end 26.

Projecting from dispensing end 28 of body 20 is an elongated stem 34. Stem 34 has a transverse cross section with a diameter that is smaller than the diameter of the transverse cross section of body 20. As discussed below, stem 34 is configured to receive and engage needle shield 18. Syringe barrel 12, or at least body 20, is made of a transparent or semi-transparent material such as clear plastic or glass.

Projecting from stem 34 of syringe barrel 12 along a central longitudinal axis 37 of body 20 is a tubular needle 36. Needle 36 has a proximal end 33 that communicates with compartment 30 of syringe barrel 12 and an opposing distal end 35 that terminates at a sharpened tip 38. Needle 36 is typically made of metal. In the embodiment depicted, needle 36 is permanently attached to syringe barrel 12 such as by being molded into stem 34 or by being attached with an adhesive. In alternative embodiments, needle 36 can be removably attached to syringe barrel 12. For example, stem 34 and needle 36 can be formed with complementary halves of a luer-lock connection that permit fluid coupling therebetween. Other types of connection can also be used.

As also depicted in FIG. 2, needle shield 18 has a first end 40 for attaching to stem 34 of syringe barrel 12 and an opposing second end 42 that terminates at a terminal end face 48. Needle shield 18 has an interior surface 43 that bounds a cavity 44 that is open at first end 40. Cavity 44 is configured to receive stem 34 so that a friction tight engagement is formed between interior surface 43 and stem 34. When needle shield 18 is attached to syringe barrel 12, needle 36 is safely enclosed within cavity 44. Needle shield 18 typically has a portion comprised of a rigid plastic and a more flexible or elastomeric portion that engages with stem 34. In alternative embodiments, a mechanical connection can be used to secure needle shield 18 to syringe barrel 12. For example, needle shield 18 and stem 34 can be formed with complementary halves of a luer-lock connection that permit coupling therebetween. Other types of connection can also be used.

Continuing with FIG. 2, slidably disposed within compartment 30 of syringe barrel 12 is stopper 14. Stopper 14 has an annular side face 50 that extends between a proximal end face 52 and an opposing distal end face 54. Encircling and radially outwardly projecting from side face 50 are a plurality of lip seals 56. Lip seals 56 maintain a liquid tight seal against interior surface 22 of syringe barrel 12 as stopper 14 longitudinally moves within compartment 30. Accordingly, as stopper 14 advances towards dispensing end 28 of syringe barrel 12, any liquid within compartment 30 is dispensed out through stem 34 and needle 36. Centrally formed on proximal end face 52 is a threaded socket 58. Stopper 14 is typically comprised of an elastomeric material that enables a sealed engagement between stopper 14 and syringe barrel 12. Other materials that will achieve the desired functional operation can also be used.

Returning to FIG. 1, plunger rod 16 comprises an elongated shaft 62 that extends between a proximal end 64 and an opposing distal end 66. In the embodiment depicted, shaft 62 has a substantially X-shaped transverse cross section that is comprised of two elongated rails 67A and B that bisect each other at right angles along their length. Disposed at proximal end 64 of shaft 62 is a thumb rest 68. Formed at distal end 66 of shaft 62 is an end plate 70. End plate 70 has a distal end face 72 from which a threaded stem 74 centrally projects in alignment with a central longitudinal axis 76 of plunger rod 16. Threaded stem 74 is configured to thread into socket 58 of stopper 14 (FIG. 2) so that distal end face 72 sits flush against proximal end face 52 and so that stopper 14 is securely connected to plunger rod 16. Plunger rod 16 is typically molded from a polymeric material.

Figure 3:
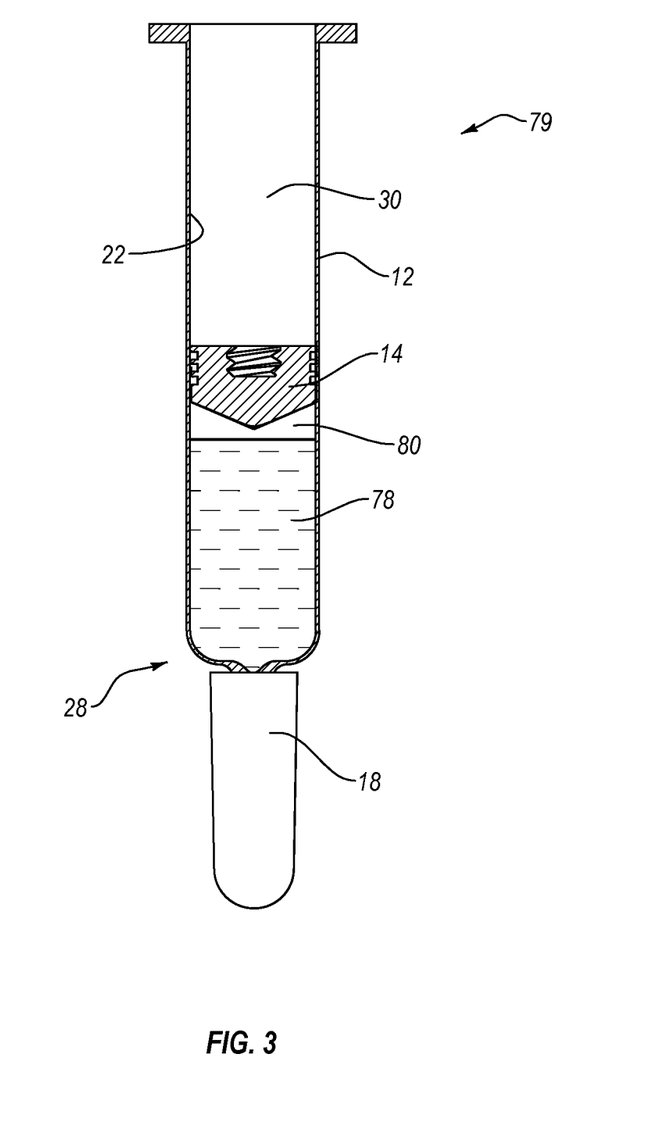
FIG. 3 is an elevated side view of a pre-loaded syringe barrel incorporating the syringe barrel, stopper and needle shield shown in FIG. 2.

The present invention is primarily directed towards methods and systems for attaching plunger rod 16 to stopper 14 when syringe 10 is in a partial pre-assembled condition. Specifically, FIG. 3 shows a pre-loaded syringe barrel 79 that comprises syringe barrel 12, needle shield 18 secured to dispensing end 28, stopper 14 disposed within compartment 30 of syringe barrel 12, and a liquid dosage 78 disposed within compartment 30 between stopper 14 and needle shield 18. Dosage 78 can comprise a drug or a placebo, such as a saline solution. Often, although not always, air bubbles 80 can also be located with compartment 30 between stopper 14 and needle shield 18.

Figure 4:
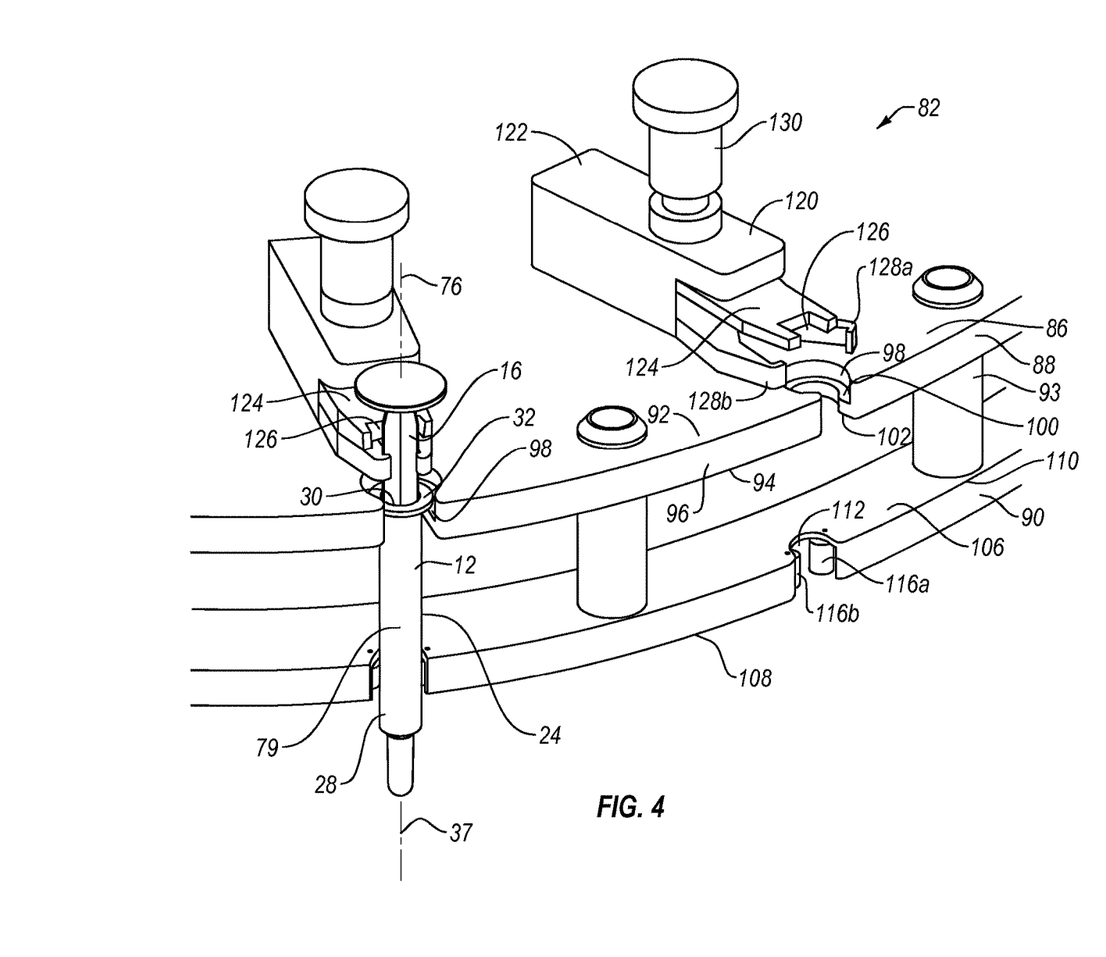
FIG. 4 is a perspective view of a syringe assembler used for attached the plunger rod to the pre-loaded syringe barrel shown in FIG. 3.

A syringe assembler is typically used for coupling plunger rod 16 to stopper 14 of pre-loaded syringe barrel 79. Depicted in FIG. 4 is one embodiment of a syringe assembler 82 incorporating features of the present invention. Syringe assembler 82 comprises a platform 86 on which pre-loaded syringe barrel 79 is selectively mounted. Platform 86 can comprise a stationary platform, a shuttle platform that moves back and forth between two or more stations, a carousel that rotates between two or more stations or other platform configurations. In the embodiment discussed below, platform 86 is discussed as comprising a rotatable carousel. However, other platform configurations can also be used. Platform 86 can be progressively rotated between a plurality of different stations where different processing steps are accomplished. In one embodiment, platform 86 can be rotated through a range of two to fifteen different stations with six to twelve stations being more common. Other numbers of stations can also be used.

Platform 86 comprises an upper platform 88, a spaced apart lower platform 90 and supports 93 that extend therebetween. Upper platform 88 has a top surface 92 and an opposing bottom surface 94 with and outside face 96 that extends therebetween. A plurality of openings 98 extend through upper platform 88 between surfaces 92 and 94 at spaced apart intervals adjacent to outside face 96. Radially inwardly projecting into each opening 98 is a shoulder 100. Opening 98 is configured to receive syringe barrel 12 so that flange 32 rests on top of shoulder 100. A channel 102 laterally extends through outside face 96 to communicate with opening 98. Channel 102 is configured so that syringe barrel 12 can be laterally slid through channel 102 and into opening 98. However, channel 102 is not large enough to allow flange 32 to laterally pass therethrough. As such, once flange 32 is resting on shoulder 100, syringe barrel 12 cannot accidentally slide out through channel 102.

Lower platform 90 also has a top surface 106 and an opposing bottom surface 108 and an outside face 110 extending therebetween. A plurality of spaced apart notches 112 are recessed on outside face 110 so as to extend between top surface 106 and bottom surface 108. Each notch 112 is vertically aligned with a corresponding opening 98 and is configured to receive dispensing end 28 of syringe barrel 12. With regard to each notch 112, mounted on bottom surface 108 is a pair of freely rotatable wheels 116A and B. Wheels 116 are disposed on opposing sides of notch 112 and are placed so that exterior surface 24 of syringe barrel 12 either rest directly against or is disposed directly adjacent to wheels 116 when syringe barrel 12 is received within opening 98. When syringe barrel 12 is positioned within opening 98 so that flange 32 rests on shoulder 100 and within notch 112, syringe barrel 12 is still free to rotate about its longitudinal axis 37.

A retainer 120 is mounted on top surface 92 of upper platform 88 and is used to secure plunger rod 16 in a desired vertical orientation so that plunger rod 16 can freely side vertically up and down but is precluded from rotating about its longitudinal axis 76. Specifically, retainer 120 comprises a housing 122 mounted on top surface 92 of upper platform 88. Projecting from housing 122 is an alignment rail 124 having a notch 126 formed on the end thereof that is vertically aligned with opening 98. A pair of arms 128A and B are pivotably mounted to housing 122 and are movable between an open position and a closed position, as shown in FIG. 4. In the opened positioned, the free ends of arms 128A and B are separated onto opposing sides of opening 98. In the closed position, the free ends of arms 128A and B are closed towards each other so that they can capture the opposing sides of one of rails 67A or B of plunger rod 16 therebetween. Arms 128A and B engage plunger rod 16 so that plunger rod 16 can freely side vertically up and down but is precluded from rotating about longitudinal axis 76. A lock 130 engages with arms 128A and B so as to securely hold them in the closed position.

Figure 5:
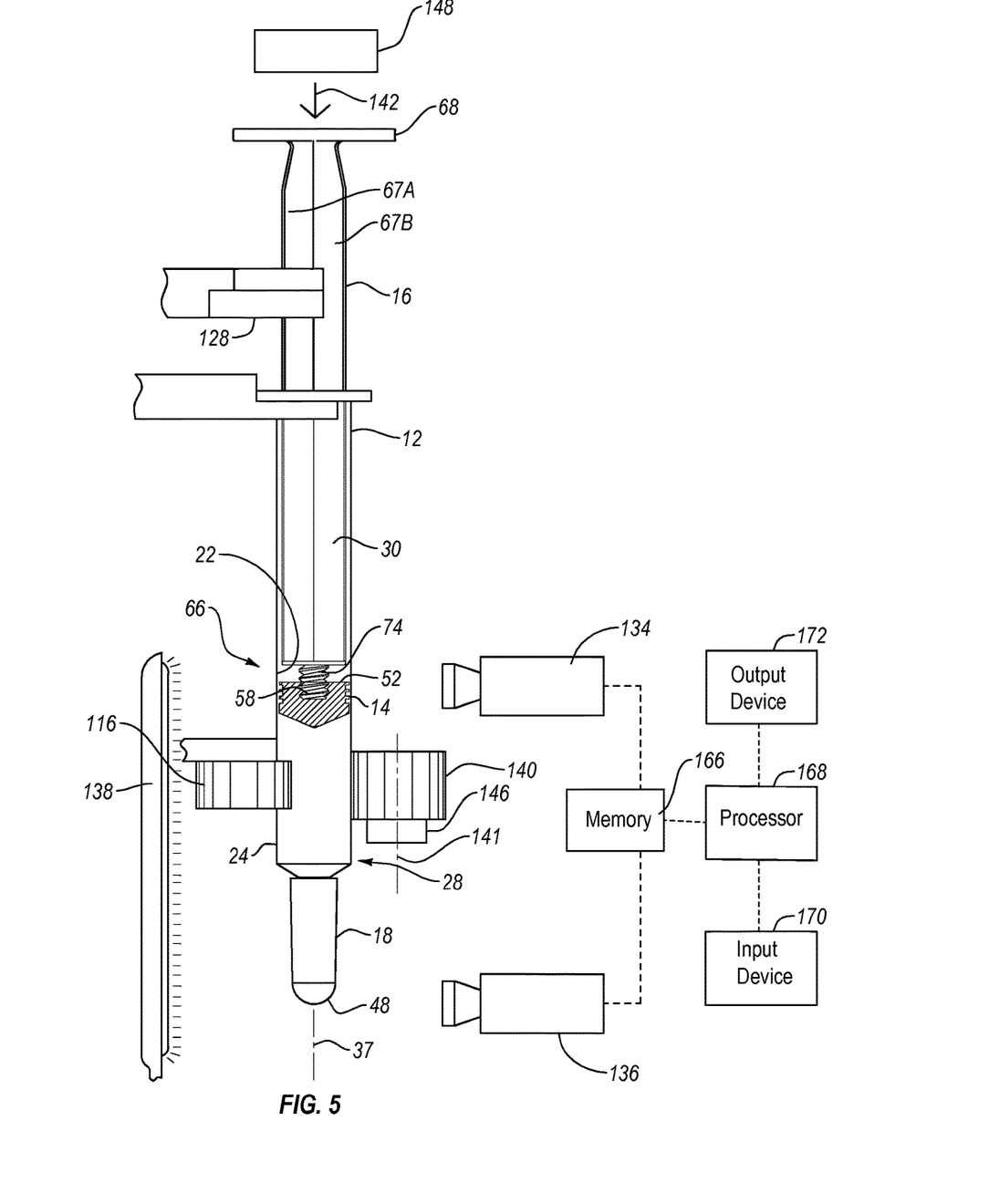
FIG. 5 is an elevated side view of an assembly station of the syringe assembler wherein the plunger rod is received within the syringe barrel but is not attached to the stopper.

During use, pre-loaded syringe barrel 79 is received within an opening 98 at a first station of syringe assembler 82 so that flange 32 rests on shoulder 100 and so that dispensing end 28 is disposed within notch 112 against or directly adjacent to wheels 116. In this position, pre-loaded syringe barrel 79 is partially secured to platform 86 but is free to rotate about longitudinal axis 37. Plunger rod 16 is aligned within notch 126 of alignment rail 124 and distal end 66 thereof is vertically advanced downward and into compartment 30 of syringe barrel 12. When distal end 66 comes to rest on stopper 14, as shown in FIG. 5, arms 128A and B are moved into the closed position so as to engage plunger rod 16. In this position, threaded stem 74 of plunger rod 16 is vertically aligned with and disposed directly against threaded socket 58 of stopper 14. As a result of the engagement with arms 128A and B, plunger rod 16 is precluded from rotating about is longitudinal axis but is still free to slide vertically up and down along its longitudinal axis.

With plunger rod 16 so locked, the carousel/platform 86 is rotated/moved so that pre-loaded syringe barrel 79 with plunger rod 16 are moved to the next station which is referred to herein as the assembly station. At the assembly station, as depicted in FIG. 5, syringe assembler 82 is shown as further comprising a mechanically driven drive wheel 140 that is selectively pressed against exterior surface 24 of syringe barrel 12 so as to push syringe barrel 12 against wheels 116A and B. Drive wheel 140 is typically disposed horizontal to wheels 116 and is comprised of or has an outside layer that comprises a material that will firmly grip syringe barrel 12, such as an elastomer. In this configuration, select rotation of drive wheel 140 facilitates rotation of pre-loaded syringe barrel 79 relative to plunger rod 16. This rotation of pre-loaded syringe barrel 79 relative to plunger rod 16 is used to thread stem 74 of plunger rod 16 into threaded socket 58 of stopper 14.

Operable with drive wheel 140 is a torque regulator 146. Torque regulator 146 is used to adjustably set the torque at which drive wheel 140 can rotate. Accordingly, as will be discussed below further, torque regulator 146 can be set so that drive wheel 140 can only apply up to a pre-defined torque to pre-loaded syringe barrel 79. As a result, pre-loaded syringe barrel 79, i.e., namely stopper 14, is limited to only applying a pre-defined torque to plunger rod 16. As discussed above, syringe assembler 82 is configured so that plunger rod 16 and stopper 14 can be threaded together with no movement or only limited movement of stopper 14 relative to syringe barrel 12. Stopper 14 is held relative to syringe barrel 12 by frictional engagement. As stopper 14 is threaded onto plunger rod 16, the torque applied by stopper 14 (through drive wheel 140 and syringe barrel 12) progressively increases as threaded stem 74 of plunger rod 16 threads into threaded socket 58 of stopper 14. During operation, torque regulator 146 can be set so that the maximum torque applied by stopper 14 to plunger rod 16 through drive wheel 140 is less than the force required to overcome the static friction between stopper 14 and syringe barrel 12. Once drive wheel 140 reaches the pre-defined torque, the drive mechanism rotating drive wheel 140 can be deactivated, thereby assisting to ensure no movement of stopper 14 relative to syringe barrel 12 while stopper 14 and plunger rod 16 are threaded together.

One embodiment of the present invention also includes means for applying a force 142 longitudinally along plunger rod 16. Force 142, as depicted in FIG. 5, is sufficient to require plunger rod 16 to slide toward stopper 14 as stem 74 of plunger rod 16 is threaded into socket 58 of stopper 14. Force 142 is primarily needed to help start the threaded engagement between stem 74 and socket 58. Once the threaded engagement is started, rotation of stopper 14 causes plunger rod 16 to be pulled toward stopper 14. Force 142 is less than the force required to overcome the static friction between stopper 14 and syringe barrel 12. Accordingly, force 142 is sufficiently small so that it does not cause movement of stopper 14 relative to syringe barrel 12 while stopper 14 and plunger rod 16 are threaded together.

Force 142 can be applied in variety of different ways. For example, one embodiment of the means for applying force 142 can be a weight 148 that is placed on top of thumb rest 68. Weight 148 can be retained by a guide so that weight 148 does not fall off during movement of plunger rod 16 and remains centrally positioned. In other embodiments, a mechanical, pneumatic, or other type of press can be applied to plunger rod 16 to production force 142. The amount of force 142 depends upon a variety of factors including the size of syringe barrel 12 and stopper 14. In one embodiment, the weight load applied to plunger rod 16 is in a range between about 40 grams to about 150 grams with about 50 grams to about 100 grams being more common. Other forces can also be applied.

Continuing with FIG. 5, syringe assembler 82 further comprises a first camera 134 positioned so as to be horizontally disposed to stopper 14 and a second camera 136 positioned so as to be horizontally disposed to needle shield 18. Electronically coupled with cameras 134 and 136 is a memory 166 for storing digital images from the cameras, a computer processor 168 for processing information from the digital images, an input device 170, such as a keyboard, touch screen, or the like, for programming and/or delivering commands to cameras 134/136 and/or computer processor 168, and an output device 172, such as a display screen, printer or the like, for displaying data, images, and other output from cameras 134/136 and/or computer processor 168. Memory 166 can comprise a hard drive, flash memory, thumb drive, EEPROM, non-volatile memory and other non-transitory computer readable media. Although memory 166 and computer processor 168 are depicted in FIG. 5 as being separate and discrete from cameras 134 and 136, in alternative embodiments memory 166 and/or computer processor 168 can be incorporated into or comprise a portion of camera 134 and/or camera 136. For example, computer processor 168 which is used to compare digital images from cameras 134 and 136, as discussed below, can comprise the computer processor that is integrated into camera 134 and/or 136 for use in the operation of the cameras. The same is also true for memory 166. A back light 138, such as in the form of a red LED or other light source, can be disposed on the opposite side of syringe barrel 12 so as to face cameras 134 and 136. Back light 138 helps to improve the resolution of the digital images taken by cameras 134 and 136.

As discussed below, cameras 134, 136, memory 166, and processor 168 are used in part to help determine if there is any movement of stopper 14 within pre-loaded syringe barrel 79 during the attachment of plunger rod 16. The determination of whether stopper 14 has moved during the attachment of plunger rod 16 is helpful in qualifying the sterility of dosage 78 within syringe barrel 12. For example, as depicted in FIG. 5, interior surface 22 of syringe barrel 12 proximal of stopper 14 is not sterile. Thus, if stopper 14 moves proximally within syringe barrel 12 a sufficient distance, dosage 78 within syringe barrel 12 can become contaminated and thus unfit for use. This movement of stopper 14 can result from plunger rod 16 being moved proximally when attached to stopper 14. Alternatively, stopper 14 may be moved distally which compresses gas bubbles 80 within syringe barrel 12. In turn, the compressed gas can act as a spring that then pushes stopper 14 proximally outside of the sterile zone. Stopper 14 can also be moved through other causes. Thus, it is useful to monitor any movement of stopper 14 relative to syringe barrel 12 during the entire process of attaching plunger rod 16 to stopper 14.

If stopper 14 moves distally or proximally relative to syringe barrel 12 by more than a predefined movement tolerance, the syringe and corresponding dosage is rejected and disposed of. The length of the predefined movement tolerance of stopper 14 is dependent upon the size of syringe barrel 12, stopper 14 and other relevant factors. Typically, however, the movement tolerance is less than 1 mm and more commonly less than 0.8 mm or 0.6 mm, either proximally or distally within syringe barrel 12. Other dimensions can also be used. Because dosage 78 within a single syringe can be very expensive, at times ranging from hundreds of dollars to thousands of dollars, it is prudent to ensure both that dosage 78 is not contaminated due to excessive movement of stopper 14 relative to syringe barrel 12 and that no dosage 78 is unnecessarily rejected due to a false reading of movement of stopper 14 relative to syringe barrel 12.

Figure 6:
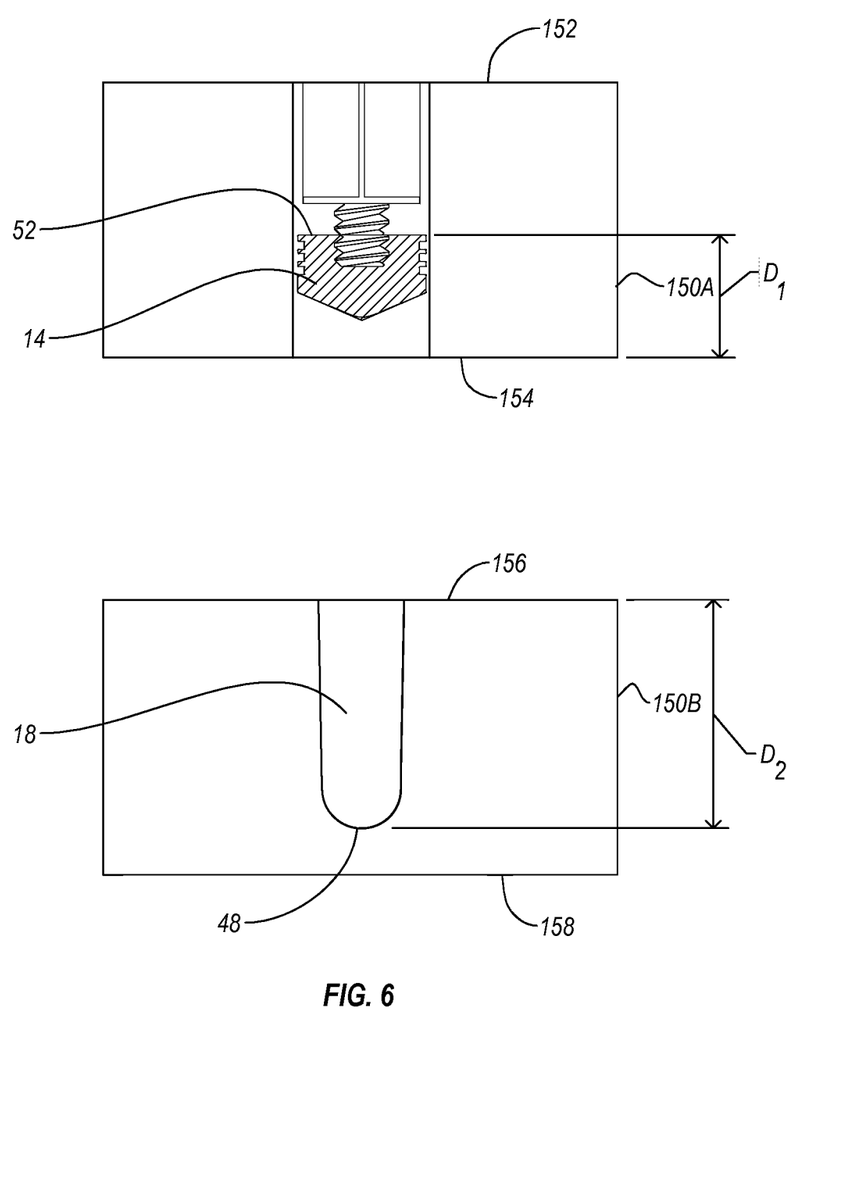
FIG. 6 is a front view of an initial digital image of the stopper taken by a first camera of the syringe assembler and an initial digital image of the needle shield taken by a second camera of the syringe assembler.

During operation, with pre-loaded syringe barrel 79 and plunger rod 16 positioned at the assembly station, as depicted in FIG. 5, camera 134 takes an initial digital image 150A, as depicted in FIG. 6, while camera 136 concurrently takes an initial digital image 150B. Initial digital images 150A and 150B are taken prior to the application of force 142 or the rotation of pre-loaded syringe barrel 79 and provide an initial fixed reference point for stopper 14 and syringe barrel 12. These initial digital images 150 can be taken prior to, after, or during the insertion of plunger rod 16. Image 150A has an upper border 152 and an opposing lower border 154 and depicts therein at least a portion of stopper 14, including proximal end face 52. Image 150B also includes an upper border 156 and a lower border 158 and depicts at least a portion of needle shield 18, including terminal end face 48. Processor 168 is programmed to analyze initial digital image 150A and determine the number of pixels that extend along a line from proximal end face 52 of stopper 14 to lower border 154 of initial digital image 150A. This information is used to calculate an initial value $V_{1C1}$ (first value from first camera) for camera 134 that is stored in memory 166 and represents a linear distance $D_1$ between proximal end face 52 of stopper 14 and lower border 154 as shown in the top half of FIG. 6.

Likewise, processor 168 analyzes initial digital image 150B and determines the number of pixels that extend along a line from terminal end face 48 of needle shield 18 to upper border 156 of initial digital image 150B. This information is used to calculate a first value $V_{1C2}$ (first value from second camera) for camera 136 that is stored in memory 166 and represents a linear distance $D_2$ between terminal end face 48 of needle shield 18 and upper border 156 as shown in the bottom half of FIG. 6. To enable cameras 134 and 136 to capture the desired digital images with the needed resolution, camera 134 is typically horizontally spaced apart from stopper 14 and camera 136 is typically spaced apart from needed shield 18 or syringe barrel 12 at a distance between 150 mm to 250 mm with 170 mm to 220 mm being more common. Other dimensions can also be used.

Because cameras 134 and 136 are held stationary at fixed locations, for all subsequent digital images taken by cameras 134 and 136, lower border 154 and upper border 156 are always at the exact same location (within acceptable tolerances). That is, for all digital images taken by cameras 134 and 136, borders 154 and 156 are common fixed locations. Accordingly, for further digital images taken by camera 134 at different points in time during the assembly process, processor 168 can again calculate values from each further digital image that represent the linear distance from proximal end face 52 of stopper 14 to lower border 154, i.e., values $V_{2C1}$, $V_{3C1}$, $V_{4C1}$ etc., which values are also stored in memory 166. Processor 168 can then compare each of the further value $V_{2C1}$, $V_{3C1}$, $V_{4C1}$ etc. against initial value $V_{1C1}$. If the compared values are the same, stopper 14 has not moved relative to its initial position. However, if the compared values are different, stopper 14 has moved relative to its initial position.

Although comparing calculated values $V_{2C1}$, $V_{3C1}$, ... to $V_{1C1}$ is helpful to know whether stopper 14 has moved relative to its original position, such information is not conclusive as to whether stopper 14 has moved relative to syringe barrel 12. For example, if both syringe barrel 12 and stopper 14 concurrently move upward or downward during the attachment of plunger rod 16, comparing the later values of $V_{2C1}$, $V_{3C1}$, . . . to initial value $V_{1C1}$ would show that stopper 14 has moved and thus may be interpreted that stopper 14 has moved relative to syringe barrel 12. Such an interpretation, however, would be wrong and could result in an unwarranted disposal of the syringe and corresponding dosage. Furthermore, during the attachment of plunger rod 16, syringe barrel 12 may move one direction while stopper 14 moves a corresponding amount in the opposite direction. In this case, comparing later values $V_{2C1}$, $V_{3C1}$, . . . to initial $V_{1C1}$ would incorrectly reflect that stopper 14 has not moved. As such, a potentially contaminated dosage may not be rejected.

Taking digital images from camera 136 concurrently with taking digital images from camera 134 resolves the above concerns. That is, the value $V_{1C2}$ reflects the position of needle shield 18 and syringe barrel 12 relative to a fixed point. Comparing the further later values $V_{2C2}$, $V_{3C2}$, $V_{4C2}$ etc. to initial $V_{1C2}$ determines if there has been any movement of needle shield 18/syringe barrel 12 relative to their initial position. By determining the amount stopper 14 has moved relative to its initial position, i.e., comparing $V_{2C1}$ to $V_{1C1}$, and by determining at the same point in time the amount that needle shield 18/syringe barrel 12 have moved relative to their initial position, i.e., comparing $V_{2C2}$ to $V_{1C2}$, it can accurately be determined the amount that stopper 14 has moved relative to syringe barrel 12. For example, if stopper 14 has moved proximally up 0.5 mm relative to its initial position and needle shield 18/syringe barrel 12 have moved distally down 0.2 mm relative to their initial position, stopper 14 has moved upward 0.7 mm relative to syringe barrel 12. This calculated movement of stopper 14 relative to syringe barrel 12 can then be compared to the predefined movement tolerance for movement of stopper 14 to determine whether or not the syringe and the corresponding dosage should be rejected or approved for further processing.

Figure 7:
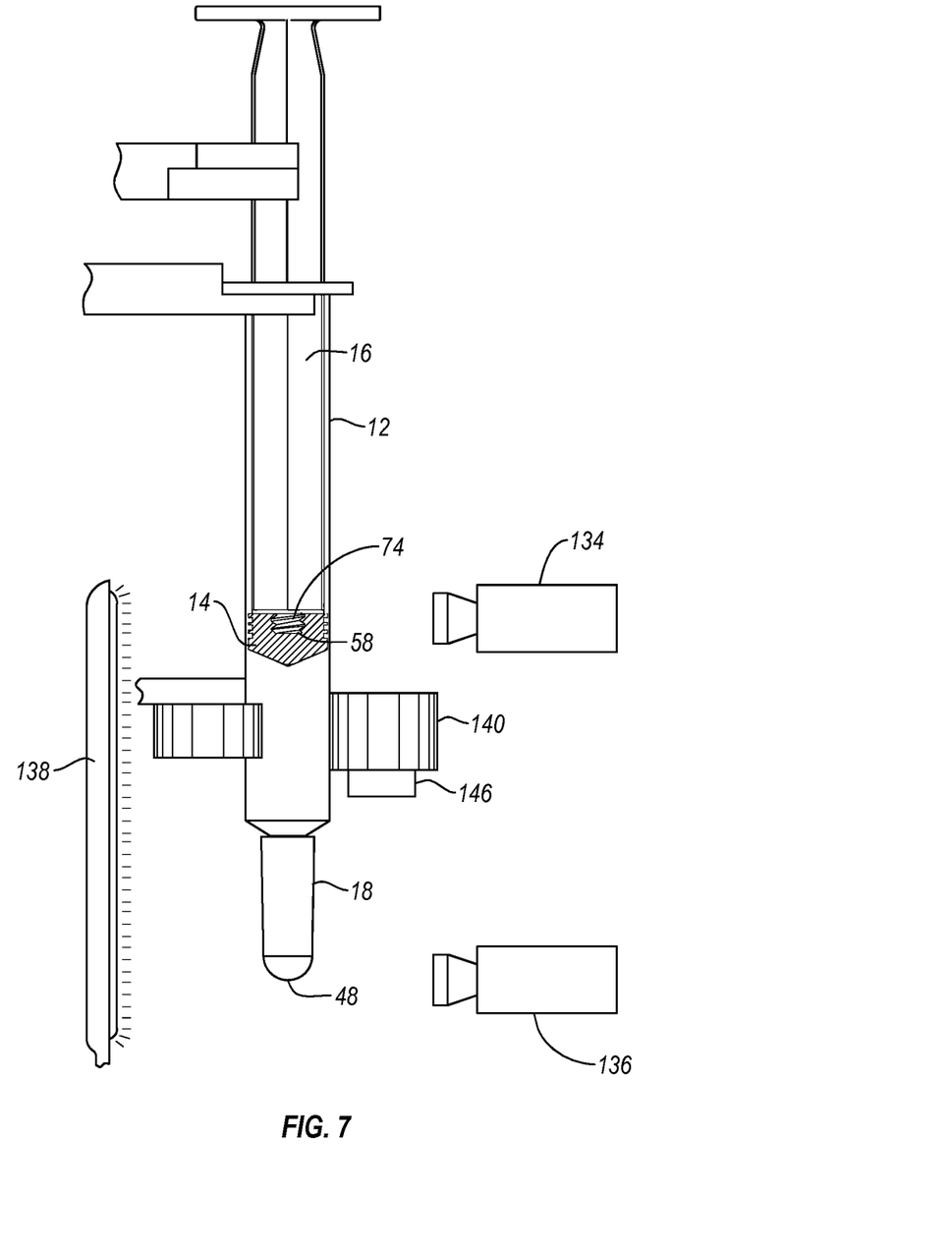
FIG. 7 is an elevated side view of the assembly station of the syringe assembler shown in FIG. 5 wherein the plunger rod is attached to the stopper.

During operation, once the initial digital images are taken so that values $V_{1C1}$ and $V_{1C2}$ can be determined, force 142 is applied to plunger rod 16 and drive wheel 140 is activated. As discussed above, drive wheel 140 causes the rotation of syringe barrel 12 and stopper 14 so that stem 74 is threaded into socket 50, as shown in FIG. 7. Stem 74 continues to thread into socket 58 until drive wheel 140 reaches the pre-defined torque value regulated by torque regulator 146. At that point, drive wheel 140 is deactivated. During the time interval between the taking of the initial digital images and the deactivation of drive wheel 140, cameras 134 and 136 can each concurrently take any desired number of further digital images. The number of further digital images is typically in a range between 1 to 10 with 2 to 8 or 3 to 7 being more common. Other numbers can also be taken. Typically there is at least a plurality of further digital images taken which is typically at least two pairs and more commonly at least three or four. The further digital images can be taken at any desired stage during the attachment of plunger rod 16 to stopper 14. For example, one or more digital images can be taken: during and/or after the application of force 142 but prior to the start of rotation of drive wheel 140, during the rotation of drive wheel 140, upon completion of the rotation of drive wheel 140, during and/or after the removal of force 142 and at other points during the attachment process.

Using the process as discussed above, for each pair of further digital images taken, that values $V_{2C1}$, $V_{3C1}$, . . . and $V_{2C2}$, $V_{3C2}$, . . . are calculated and then compared to initial values $V_{1C1}$ and $V_{1C2}$, respectively, to determine if there has been any movement of stopper 14 relative to plunger rod 16. By taking a plurality of digital images during the attachment process, the system is also able to account for temporary displacement of stopper 14 relative to syringe barrel 12. For example, if during the attachment process stopper 14 is initially displaced relative to syringe barrel 12 but then again returns to its original position by the end of the attachment process, simply taking digital images at the start and at the end of the process would miss movement of stopper 14 relative to syringe barrel 12, thereby failing to reject the syringe and corresponding dosage. Taking and comparing multiple digital images throughout the attachment process ensures that there is no movement of stopper 14 at any time during the attachment process that would require the rejection of the syringe.

Figure 8:
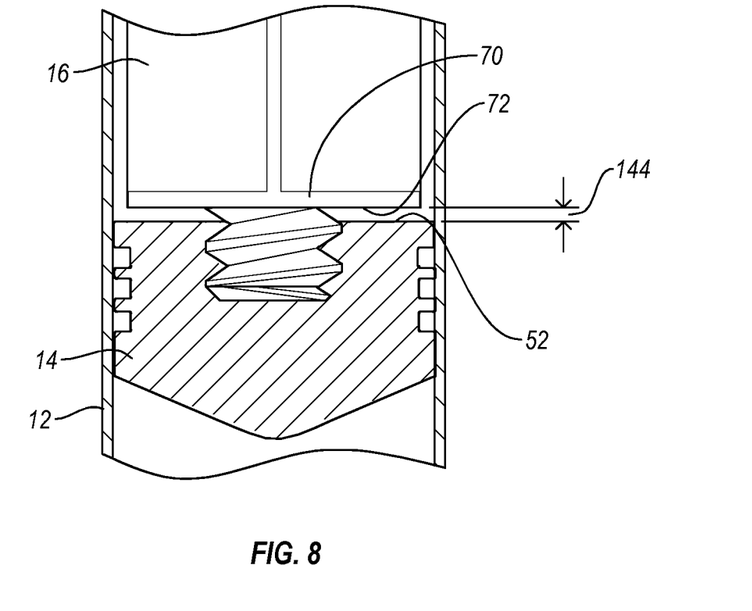
FIG. 8 is an enlarged, partial cross-sectional side view of the plunger rod attached to the stopper where a gap exists between the plunger rod and the stopper.

In one embodiment, digital images are taken by cameras 134 and 136 directly after drive wheel 140 has ceased rotating as a result of reaching the predefined torque value. In addition to comparing the calculated values from these further digital images to the initial values $V_{1C1}$ and $V_{1C2}$ to determine if there has been any movement of stopper 14 relative to syringe barrel 12, the further digital image from camera 134 can also be used to detect whether a gap 144, as depicted in FIG. 8, remains between proximal end face 52 of stopper 14 and distal end face 72 of plunger rod 16. Again, processor 168 can be used to measure the width of gap 144 by counting the number of pixels in a digital image taken by camera 134 that extend along a linear line passing from proximal end face 52 of stopper 14 to distal end face 72 of plunger rod 16. Back light 138 (FIG. 7) is particularly helpful in illuminating gap 144 so that the width thereof can be calculated.

Gap 144 can be undesirable for a couple of different reasons. For example, if plunger rod 16 is not fully threaded onto stopper 14, it is possible that plunger rod 16 could unintentionally unscrew and become detached from stopper 14. More problematic, however, is that in some embodiments the needle safety device that is used with syringe 10 is calibrated based on the placement of plunger rod 16. If plunger rod 16 is not fully threaded into stopper 14, the needle safety device may not operate properly. Other problems can also arise from having a large gap 144.

Processor 168 compares the calculated width for gap 144 to a predetermined gap tolerance. If the calculated width is within the gap tolerance, the process continues normally. However, if the calculated width is outside of the gap tolerance, the syringe and corresponding dosage can either be rejected and disposed of or attempts can be made to further thread stopper 14 onto plunger rod 16 so as decrease gap 144. In one embodiment, the predefined tolerance for gap 144 can be less then 0.5 mm and more commonly less than 0.3 mm. Other dimensions can also be used based on the size of the syringe barrel, the size of the stopper and other variables.

In one approach to decrease the width of gap 144, processor 168 is used to calculate the angle over which preloaded syringe barrel 79 (including stopper 14) must be rotated relative to plunger rod 16 so that stem 74 of plunger rod 16 threads sufficiently far into socket 58 of stopper 14 to decrease gap 144 to within the predefined gap tolerance. The angle of rotation can be calculated based on the width of gap 144 and the pitch on the threads of stem 74 and socket 58. Once the angle is calculated, torque regulator 146 is deactivated and pre-loaded syringe barrel 79 is rotated by drive wheel 140 over the calculated angle. During and/or after the further rotation of syringe barrel 12 over the calculated angle, further digital images are again taken from cameras 134 and 136. Using the same methods as discussed above, these further digital images are used to determine: 1) if the gap 144 is now within the predefined gap tolerance and 2) whether stopper 14 moved relative to syringe barrel 12 beyond the predefined movement tolerance.

If gap 144 is within the predefined gap tolerance and any movement of stopper 14 is within the predefined movement tolerance, normal processing on the syringe is continued. However, if gap 144 is still outside of the predefined gap tolerance, the above process of rotating syringe barrel 12 and stopper 14 over a calculated angle can again be repeated. However, once stopper 14 moves by more than the predefined movement tolerance, the syringe and corresponding dosage are marked as rejected and are subsequently removed from platform 86 and disposed of By using the above process to reduce gap 144, a higher percentage of processed syringes are able to be certified as meeting predefined processing conditions and thus approved for use. The process thus helps to eliminate unnecessary waste of syringes and the dosages therein.

Following the process to decrease the width of gap 144, if needed, force 142 is removed from plunger rod 16 and drive wheel 140 is removed from syringe barrel 12. After the removal of force 142, final digital images can be taken from cameras 134 and 136. Again, values based on these final digital images are compared to initial values $V_{1C1}$ and $V_{1C2}$ to determine if there has been any movement of stopper 14 relative to syringe barrel 12. Carrousel/platform 86 can then be rotated/moved so that the assembled syringe is moved to the next processing station. If stopper 14 has moved beyond the movement tolerance, the syringe is removed from platform 86 and disposed of at this next station. Otherwise, the syringe continues its normal processing and the assembled syringe is eventually packaged for subsequent use.

It is appreciated that the process of determining whether stopper 14 has moved relative to syringe barrel 12 can be accomplished in a variety of different ways. For example, it is not necessary that the compared values be based on the location of proximal end face of stopper 14 or terminal end face 48 of needle shield 18. Although these surfaces are easily detected because they are openly exposed on one side, the values can also be based on the locations of other structural features on stopper 14, syringe barrel 12 or needle shield 18. In addition, rather than being based on structural features, the measured values can be based on markings or other identifies that are printed on, attached to, or embedded within stopper 14, syringe barrel 12 and/or needle shield 18. Furthermore, the reference points on the digital images can be the upper border, the lower border or some other fixed reference point that is common to all digital images taken by the corresponding camera.

In some embodiments, it is appreciated that the compared values can be generated from a single digital image. For example, the initial values and the later values that are compared could comprise the distance from proximal end face 52 or from some other structure or marking on stopper 14 to lower border 154 of the digital image while the other value generated from the same digital image could comprise the distance from a marking or other identifier located on syringe barrel 12 to lower border 154 of the digital image. These two values generated from a single digital image can be used to determine whether stopper 14 has moved relative to syringe barrel 12.

In another embodiment, camera 134 can take a single digital image that shows both a fixed point on stopper 14 (such as proximal end face 52 or some other structure or marking on stopper 14) and a fixed point on syringe barrel 12 (such as a structural feature or some marking on syringe barrel 12). Processor 168 can then be used to calculate the distance between the two fixed points. By comparing this value with corresponding values generated from later taken digital images, it can again be determined whether stopper 14 has moved relative to syringe barrel 12. It is appreciated that there are still other ways based on digital images to determine whether stopper 14 moves relative to syringe barrel 12 during the attachment of plunger rod 16 to stopper 14. However, there are some benefits to using the above initially described process that incorporates both cameras 134 and 136. For example, by using the initially described process, the system can be used with virtually all traditional type of pre-loaded syringe barrels, i.e., neither the syringe barrel, stopper, nor the needle shield need to be specially manufactured. Furthermore, the process is easily implemented and operated with a high degree of accuracy.

It is appreciated that reducing gap 144 can also be accomplished in different ways. For example, in contrast to calculating the angle over which preloaded syringe barrel 79 can be further rotated to close gap 144, the setting for torque regulator 146 could be adjusted so that it is closer to the force that will overcome the static friction between stopper 14 and syringe barrel 12. Drive wheel 140 can then again be operated to the increased level of torque. Further digital images can then be taken to determine whether or not gap 144 is within the gap tolerance and whether stopper 14 has moved beyond the movement tolerance. Other methods can also be used.

In yet another alternative embodiment, in contrast to holding plunger rod 16 stationary and rotating syringe barrel 12, syringe barrel 12 can be held stationary while plunger rod 16 is rotated, such as through the use of a robotic arm. A force can be applied to either move plunger rod 16 down or move syringe barrel 12 up as plunger rod 16 and stopper 14 are screwed together.

As discussed above, the inventive system has a number of unique benefits. For example, the system enables a correct determination of whether stopper 14 has moved relative to syringe barrel 12 while at the assembly station independent of whether there has been some movement of syringe barrel 12. Furthermore, the system enables the determination of whether stopper 14 has moved relative to syringe barrel 12 while at the assembly station even if stopper 14 returns to its original position. In addition, the system detects the gap distance between the plunger rod and the stopper to ensure proper coupling therebetween. Likewise, the system provides a mechanism for closing gap distances that are too large, thereby preserving more syringes, while still ensuring no unwanted movement of stopper 14 relative to syringe barrel 12.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for assembling a syringe, the method comprising:
   supporting a syringe barrel that bounds a compartment extending between a loading end and an opposing dispensing end, a stopper being movably disposed with the compartment of the syringe barrel with a liquid dosage being disposed within the compartment between the stopper and the dispensing end;
   inserting a distal end of a plunger rod into the compartment of the syringe barrel at the loading end thereof;
   taking an initial digital image of the stopper within the syringe barrel either before, during or after inserting the distal end of the plunger rod into the compartment of the syringe barrel;
   coupling the distal end of the plunger rod to the stopper located within the compartment of the syringe barrel so that the plunger rod is secured to the stopper;
   taking a plurality of further digital images of the stopper within the syringe barrel during or after coupling the distal end of the plunger rod to the stopper; and
   comparing information determined from each of the further digital images to information determined from the initial digital image using a computer processor to determine if the stopper in each of the further digital images has moved relative to the syringe barrel.

2. The method as recited in claim 1, wherein the step of taking the plurality of further digital images comprises:
   taking a first further digital image of the stopper within the syringe barrel during coupling the distal end of the plunger rod to the stopper; and
   taking a second further digital image of the stopper within the syringe barrel after coupling the distal end of the plunger rod to the stopper.

3. The method as recited in claim 2, wherein the step of taking a plurality of further digital images comprises taking at least four digital images of the stopper at different times.

4. The method as recited in claim 1, wherein all of the plurality of further digital images are taken with the syringe barrel being located at the same location.

5. The method as recited in claim 1, wherein the coupling step comprises threading the stopper onto the distal end of the plunger rod.

6. The method as recited in claim 5, wherein the step of threading comprises rotating the syringe barrel and the stopper relative to the plunger rod for threading the stopper onto the distal end of the plunger rod.

7. The method as recited in claim 1, further comprising:
   packaging the assembled syringe for subsequent use if it is determined from the comparing step that any movement of the stopper is within a predefined tolerance; or
   discarding the assembled syringe and dosage if it is determined from the comparing step that the stopper has moved by more than the predefined movement tolerance.

8. The method as recited in claim 1, further comprising:
   wherein the steps of taking an initial digital image and taking a plurality of further digital images comprise using a first camera to take the digital images of the stopper and using a second camera to simultaneously take a digital image of a needle shield secured to the dispensing end of the syringe barrel; and
   wherein the step of comparing comprises the computer processor using the digital images from the first camera and the second camera to determine movement of the stopper relative to the syringe barrel.

9. A method for assembling a syringe, the method comprising:
   supporting a syringe barrel that bounds a compartment extending between a loading end and an opposing dispensing end, a stopper being movably disposed with the compartment of the syringe barrel with a liquid dosage being disposed within the compartment between the stopper and the dispensing end;
   inserting a distal end of a plunger rod into the compartment of the syringe barrel at the loading end thereof;
   taking a first pair of digital images either before, during or after inserting the distal end of the plunger rod into the compartment of the syringe barrel, the first pair of digital images comprising a first digital image of the stopper within the syringe barrel and a first digital image of a needle shield secured to the dispensing end of the syringe barrel, the first pair of digital images recording an initial position of the stopper relative to the syringe barrel;
   coupling the distal end of the plunger rod to the stopper located within the compartment of the syringe barrel so that the plunger rod is secured to the stopper;
   taking a second pair of digital images during or after coupling the distal end of the plunger rod to the stopper, the second pair of digital images comprising a second digital image of the stopper within the syringe barrel and a second digital image of the needle shield secured to the dispensing end of the syringe barrel; and
   comparing the second pair of digital images to the initial pair of digital images using a computer processor to determine if the stopper has moved relative to the initial position.

10. The method as recited in claim 9, wherein the first pair of digital images are taken simultaneously and the second pair of digital images are taken simultaneously.

11. The method as recited in claim 9, further comprising taking a third pair of digital images comprising a third digital image of the stopper within the syringe barrel and a third digital image of the needle shield, the second pair of digital images being taken during the coupling the distal end of the plunger rod to the stopper and the third pair of digital images being taken after coupling the distal end of the plunger rod to the stopper.

12. The method as recited in claim 11, wherein the syringe barrel is mounted on a carousel that is rotatable between a plurality of different stations, the first, second, and third pair of digital images all being taken while the syringe is located at a same station.

13. A method for assembling a syringe, the method comprising:
   supporting a syringe barrel that bounds a compartment extending between a loading end and an opposing dispensing end, a stopper being movably disposed with the compartment of the syringe barrel with a liquid dosage being disposed within the compartment between the stopper and the dispensing end, a distal end of a plunger rod being partially threaded into the stopper so that a gap greater than a pre-defined gap tolerance is formed between a distal end face of the plunger rod and a proximal end face of the stopper;
   calculating from a digital image of the gap an angle over which the plunger rod or syringe barrel with stopper therein must be rotated relative to the other so that the gap distance is decreased to within the predefined gap tolerance; and
   rotating the plunger rod or syringe barrel relative to the other over the calculated angle.

14. The method as recited in claim 13, further comprising:
taking one or more digital images of the stopper within the syringe barrel during or after rotating the plunger rod or syringe barrel relative to the other over the calculated angle; and
comparing information from the one or more digital images to information from an initial digital image of the stopper taken prior to rotating the plunger rod or syringe barrel by using a computer processor to determine if the stopper has moved relative to the syringe barrel.

15. The method as recited in claim 13, wherein the step of taking the one or more digital images comprises using a first camera to take the one or more digital images of the stopper and using a second camera to simultaneously take a corresponding number of digital images of a needle shield secured to the dispensing end of the syringe barrel,
wherein the step of comparing comprises the computer processor using the digital images from the first camera and the second camera to determine movement of the stopper.

* * * * *